United States Patent [19]

Ripke

[11] Patent Number: 5,166,337
[45] Date of Patent: Nov. 24, 1992

[54] PROCESS FOR THE PREPARATION OF CARBOHYDRATE SURFACTANTS

[75] Inventor: Norbert Ripke, Haltern, Fed. Rep. of Germany

[73] Assignee: Huels Aktiengesellschaft, Marl, Fed. Rep. of Germany

[21] Appl. No.: 661,205

[22] Filed: Feb. 27, 1991

[30] Foreign Application Priority Data

Feb. 28, 1990 [DE] Fed. Rep. of Germany ....... 4006192

[51] Int. Cl.$^5$ .................. C07H 1/00; C07H 15/00; C07H 3/00; C07G 3/00
[52] U.S. Cl. .................. 536/126; 536/18.6; 536/4.1; 536/18.5; 536/124; 536/120
[58] Field of Search .................. 536/126, 18.6, 18.5, 536/127, 4.1

[56] References Cited

U.S. PATENT DOCUMENTS

| | | | |
|---|---|---|---|
| 3,839,318 | 10/1974 | Mansfield | 536/18.6 |
| 4,571,306 | 2/1986 | Kozak | 536/4.1 |
| 4,663,444 | 5/1987 | Egan | 536/4.1 |
| 4,990,605 | 2/1991 | Lueders | 536/18.6 |

FOREIGN PATENT DOCUMENTS

| | | |
|---|---|---|
| 0092875 | 4/1983 | European Pat. Off. . |
| 0099183 | 6/1983 | European Pat. Off. . |
| 0092355 | 10/1983 | European Pat. Off. . |
| 0132043 | 6/1984 | European Pat. Off. . |
| 0328959 | 8/1989 | European Pat. Off. . |

OTHER PUBLICATIONS

McDaniel, Jr. et al; Reg. #H619; Pub. Apr. 1989; Prep of Alkyl Glycosides.

*Primary Examiner*—Ronald W. Griffin
*Assistant Examiner*—Louise N. Leary
*Attorney, Agent, or Firm*—Oblon, Spivak, McClelland, Maier & Neustadt

[57] ABSTRACT

An alkyl glycoside having alkyl groups of 8 to 24 carbon atoms and an average polymerization degree of 1 to 10 is prepared in one stage by reacting a saccharide and at least one alcohol of 8 to 24 carbon atoms in a reaction medium containing a non-polar solvent in the presence of an emulsifier.

12 Claims, No Drawings

PROCESS FOR THE PREPARATION OF CARBOHYDRATE SURFACTANTS

BACKGROUND OF THE INVENTION

1. Field of the Invention

The present invention relates to a one-step preparation of alkyl polyglycosides which have a surfactant nature.

DESCRIPTION OF THE BACKGROUND

Alkyl polyglycosides are nonpoisonous and readily decomposable surface-active substances. Therefore, they are very useful as washing and cleaning agents and as emulsifiers and dispersing agents. However, they exhibit the desired interfacial properties only when the alkyl groups have at least 8 carbon atoms.

Alkyl glycosides and alkyl polyglycosides with long-chain alkyl groups are generally prepared by a multi-stage synthesis. Thus, according to U.S. Pat. No. 3,219,656 a double alcohol exchange is performed to prepare the alkyl glucosides. Glucose is converted first into methyl glucoside and then into butyl glucoside. Thereafter, the glucoside is converted into the desired long chain alkyl glucoside.

A simpler two stage process is shown, for example, in EP-A 0 306 652, according to which a n-butyl glycoside is first prepared by glycosidating with n-butanol and then the butylated intermediate is reacted with a long chain alcohol to form the desired long chain alkyl polyglycoside.

According to U.S. Pat. No. 3,839,318 an alkyl oligosaccharide is prepared in a one stage reaction. However, the reaction conditions must be carefully observed. The glucose to alcohol ratio must be held within very narrow boundaries. However, it is above all necessary that the formation of water proceeds slowly and is accurately controlled. The water must be removed faster than it is formed. To separate the water, a vacuum distillation or an azeotropic distillation with small quantities of hydrocarbons can be carried out. By this procedure good conversions are obtained only when optimal conditions are maintained.

As described in US-H-619 the conversion of saccharides with long chain alcohols can also be carried out with the addition of 1 to 25 moles of N-methyl-2-pyrrolidones per mole of saccharide. The polar N-methyl-2-pyrrolidone has a high boiling point of 202° C. and is, therefore, difficult to remove by means of distillation. In addition, only alkyl glycosides can be prepared since N-methyl-2-pyrrolidone prevents polymerization into the alkyl polyglycosides. A need therefore continues to exist for an improved method of preparing alkyl polyglycosides.

SUMMARY OF THE INVENTION

Accordingly, one object of the present invention is to provide a convenient, one stage process of preparing alkyl polyglycosides with long chain alkyl groups.

Briefly, this object and other objects of the invention as hereinafter will become more readily apparent can be attained in a method of preparing alkyl polyglycosides having alkyl groups of 8 to 24 carbon atoms and an average polymerization degree of 1 to 10 by reacting, in a single stage, a saccharide and at least one alcohol of 8 to 24 carbon atoms in a reaction medium containing a non-polar solvent in the presence of an emulsifier.

DETAILED DESCRIPTION OF THE BACKGROUND

Suitable saccharides include monosaccharides such as glucose, mannose, gulose, galactose and talose, and also disaccharides and oligosaccharides having up to 10 saccharide units. The units can be 1,2, 1,3, 1,4 or 1,6 linked and further either $\alpha$ or $\beta$ linkages can exist in the saccharide units. The chains can be linear or branched. Preferably glucose is employed as the saccharide.

The alcohol reactant has 8 to 24 carbon atoms, preferably 10 to 18 carbon atoms. The alcohols can be linear. However, they can also be branched. They can be saturated or also contain olefinic double bonds. Natural or synthetic fatty alcohols or fatty alcohol mixtures can be employed. Suitable examples include decanol, 10-undecan-1-ol, dodecanol, myristyl alcohol and stearyl alcohol.

The preparation of alkyl polyglycosides from saccharides and alcohols is catalyzed by means of acids. Suitable acids include mineral acids such as sulfuric or phosphorus acid. Quite suitable acids also include organic acids such as aryl-, alkyl- or aralkyl sulfonic acids.

The product alkyl polyglycosides have an average degree of polarization ranging from 1 to 10. Low average degrees of polymerization ranging from 1.3 to 5 are preferred.

Saturated, nonsaturated, linear or branched hydrocarbons, ethers, ketones and halogenated hydrocarbons are suitable as solvents and mixtures of these solvents can also be used. Preferred solvents are hydrocarbons such as pentane, hexane, cyclohexane, octane, decane, or aromatics such as benzene, toluene, and xylene. In addition, ethers are also preferred. Suitable examples include diisopropyl ether, dibutyl ether, methyl-tert-butyl ether, tetrahydrofuran or dioxane. Solvents having a boiling point in the range of 50° to 180° C. are especially preferred.

Preferably 30 to 75% reaction solutions are prepared from the saccharides and the alcohols with the nonpolar solvents. In addition, the reaction medium may contain 4 to 100% emulsifier, with respect to the reaction components. Suitable emulsifiers include non-ionic, anionic and cationic surfactants. Other interfacial-active compounds can also be used as emulsifiers. Combinations of these substances can also be used. Suitable examples of emulsifiers include saccharose fatty acid esters, sorbitan fatty acid esters, and fatty alcohol ethoxylates. Preferably paraffin sulfonates, alkyl polyglycosides with alkyl groups having 8 to 24 carbon atoms and other carbohydrate surfactants are employed.

The reaction is preferably carried out at 60° to 160° C. A temperature range of 80° to 120° C. is especially preferred. The reaction can be carried out at normal pressure, at slightly reduced pressure and also at superatmospheric pressure.

According to the process of the invention, the saccharide and alcohol, reactants and catalyst, solvent and emulsifier are mixed and the mixture is heated to the reaction temperature. Water is optionally distilled azeotropically. When the distillation of water has ended, solvent and excess alcohol are distilled. The emulsifier can also be distilled as desired. The emulsifier can also be left in the product so that the mixture of carbohydrate, surfactant and emulsifier can be reused. Product or mixture is purified and processed according to known methods.

The emulsifier and solvent employed in the present process enable good contact between hydrophilic carbohydrates and the hydrophobic long chain alcohols. The present one stage process is technically simpler than a multistage process. In addition, it permits an alcohol wide range of alcohol to saccharide ratios and the catalyst to be added. The process yields the desired products with good conversions in high yields and good purity.

Having now generally described this invention, a further understanding can be obtained by reference to certain specific examples which are provided herein for purposes of illustration only and are not intended to be limiting unless otherwise specified.

EXAMPLE 1

In a 500 ml mixing vessel with mounted column and water separator 50 g of paraffin sulfonic acid (MARLON® PS, Hüls AG, D-4370 Marl), 10 g of glucose (56 mmol), 50 g of a mixture comprising 85% dodecanol and 15% tetradecanol (261 mmol) and 100 g of diisopropyl ether are heated to 120° C. at normal pressure. The water formed during the reaction boils azeotropically and is separated in a water separator. After 15 minutes 1 g of water has formed, whereupon the reaction is terminated by cooling to room temperature.

The solution is adjusted to pH 7 with 1 N of aqueous sodium hydroxide solution, whereupon water, diisopropyl ether and then the excess alcohol mixture are distilled. The resulting product contains less than 0.3% glucose. A yield of 14.7 g dodecyl-tetradecyl-polyglucoside 85-15 (93% of the theoretical yield) is obtained. (Average degree of polymerization, 1.6.) In this example the emulsifier also serves as the catalyst.

EXAMPLE 2

In a 1,000 ml mixing vessel with mounted column and water separator 345 g of a mixture comprising 85% dodecanol and 15% tetradecanol, 80 g dodecyl-tetradecyl-polyglucoside 85-15 (polymerization degree 1.7) and 200 g of cyclohexane are added. The acid value of the mixture is set to 2.0 mg of KOH/g with toluene-$p$-sulfonic acid. This acid value is held constant during the reaction. The solution is heated to 121° C., whereupon 21 g of glucose and 84 g of a mixture comprising 85% dodecanol and 15% tetradecanol are added continuously per hour. The fill level of the reactor is held constant by continuously withdrawing the reaction product. Solvent and catalyst are remetered to the degree they are withdrawn with the reaction mixture. Thus, uniform reaction conditions are maintained.

The reaction mixture is adjusted to pH 9 with 1 N aqueous NaOH. Then cyclohexane, water and the residual alcohol mixture are removed by means of distillation in two distillation stages. Cyclohexane and alcohol mixture are added again to the reaction.

A reaction product, which has less than 0.3% glucose, 30.5 g/h dodecyl-tetradecyl-polyglucoside 85-15 (97% of the theoretical yield) (average degree of polymerization, 1.8) is obtained as the distillation residue. During the reaction the emulsifier, i.e., the alkyl polyglucoside, does not need to be remetered, since it is continuously reformed as the reaction product.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A one-stage process for preparing an alkyl glycoside having alkyl groups of 8 to 24 carbon atoms and an average polymerization degree of 1 to 10, consisting essentially of:
   reacting a saccharide and at least one alcohol of 8 to 24 carbon atoms in the presence of an acid catalyst in a reaction medium consisting essentially of a non-polar solvent in the presence of an added emulsifier for improving the contact between the saccharide and the alcohol.

2. The process of claim 1, wherein said nonpolar solvent is a hydrocarbon or ether solvent or mixture thereof.

3. The process of claim 1, wherein the solvent has a boiling point ranging from 50° to 180° C.

4. The process of claim 1, wherein the reaction medium contains 4 to 100% emulsifier, based on the reaction components.

5. The process of claim 1, wherein the emulsifier is an alkyl polyglycoside having an alkyl group of 8 to 24 carbon atoms.

6. The process of claim 1, wherein the reaction is carried out at 60° to 160° C.

7. The process of claim 6, wherein said temperature ranges from 80° to 120° C.

8. The process of claim 1, wherein the alkyl glycoside is an alkyl polyglycoside which has an average degree of polymerization ranging from 1.3 to 5.

9. The process of claim 1, wherein said alcohol reactant has from 10 to 18 carbon atoms.

10. The process of claim 1, wherein the mixture of saccharide and alcohol is present as 30 to 75% solution in the nonpolar solvent.

11. The process according to claim 1, wherein water is removed as formed.

12. The process according to claim 1, wherein the emulsifier which is an acidic emulsifier which also serves as the acid catalyst.

* * * * *